United States Patent [19]
Shimura et al.

[11] Patent Number: 5,866,683
[45] Date of Patent: Feb. 2, 1999

[54] ISOELECTRIC POINT MARKERS FOR ISOELECTRIC FOCUSING WITH FLUORESCENCE DETECTION

[75] Inventors: Kiyohito Shimura; Kenichi Kasai, both of Tsukui-gun; Hiroyuki Matsumoto; Hisayoshi Takamoto, both of Hamakita, all of Japan

[73] Assignee: Laboratory of Molecular Biophotonics, Hamakita, Japan

[21] Appl. No.: 623,833

[22] Filed: Mar. 29, 1996

[30] Foreign Application Priority Data

Mar. 31, 1995 [JP] Japan .................................... 7-076873
Oct. 19, 1995 [JP] Japan .................................... 7-271196

[51] Int. Cl.⁶ ........................................................ C07K 7/00
[52] U.S. Cl. .......................... 530/328; 530/329; 530/330; 530/331; 530/345; 204/459; 930/280
[58] Field of Search .................... 530/328–331, 530/345; 204/459; 930/280

[56] References Cited

U.S. PATENT DOCUMENTS

| | | | |
|---|---|---|---|
| 5,245,551 | 9/1993 | Heron et al. | 364/497 |
| 5,348,633 | 9/1994 | Karger et al. | 204/180 |
| 5,439,829 | 8/1995 | Anderson et al. | 436/518 |

FOREIGN PATENT DOCUMENTS

| | | |
|---|---|---|
| 0 606 804 | 7/1994 | European Pat. Off. . |
| 2 687 680 | 8/1993 | France . |

OTHER PUBLICATIONS

Manabe, "Utilization of Microcomputer in Protein Chemistry", Chemical Field, 36:470–486 (1982).
Kai et al., "Fluorescence derivation of bioactive peptides for high–performance liquid chromatograpny", Trends in Analytical Chemistry, May, 1987, pp. 116–120.
Slais et al, "Low–molecular–mass pI markers for isoelectric focusing", Journal of Chromatography A, Feb., 1994, pp. 294–256.
Nashabeh et al, Electrophoresis vol. 14 407–16 (1993).
Kai et al., J. Chrom. A vol. 653 (1993) pp. 235–240.
Shimura et al., Electrophoresis vol. 16 pp. 1479–1484 (Aug. 1995).
Zhao et al., J. Chromat. vol. 608 (1992) pp. 239–242.
Dayhoff et al., Atlas of Protein Sequence and Structure 1972 vol. 5 pp. 89–99.

*Primary Examiner*—Cecilia J. Tsang
*Assistant Examiner*—Bennett Celsa
*Attorney, Agent, or Firm*—Pillsbury Madison & Sutro, LLP Intellectual Property Group

[57] ABSTRACT

Provided are isoelectric point(pI) markers for isoelectric focusing with fluorescence detection. The markers are fluorescence-labeled oligopeptides which comprise a fluorescence dye bonded chemically to the amino group of N-terminal amino acid of oligopeptide. The marker shows its unique and narrow pI band(peak) in electrophoresis or isoelectric focusing. The markers can be designed to have appropriate pI value, and cover wide range of pI ($3<pI<11$). Further, the markers have good storage stability. The markers can be preferably applied to the capillary isoelectric focusing with fluorescence detection due to their sharp and narrow band with strong emitted fluorescence.

18 Claims, 8 Drawing Sheets

SEQUENCE LISTING ( 1 ) GENERAL INFORMATION:

( i i i ) NUMBER OF SEQUENCES: 69

( 2 ) INFORMATION FOR SEQ ID NO:1:

( i ) SEQUENCE CHARACTERISTICS:
        ( A ) LENGTH: 9 amino acid (B) TYPE: amino acid
(D) TOPOLOGY: linear (ii) MOLECULE TYPE:peptide (xi) SEQUENCE DESCRIPTION: SEQ ID NO:1:

Arg Val Tyr Ile His Pro Phe His Leu
 1               5

(2) INFORMATION FOR SEQ ID NO:2:

(i) SEQUENCE CHARACTERISTICS:
  (A) LENGTH: 8 amino acid
  (B) TYPE: amino acid
  (D) TOPOLOGY: linear (ii) MOLECULE TYPE:peptide (xi) SEQUENCE DESCRIPTION: SEQ ID NO:2:

Asn Arg Val Tyr Val His Pro Phe
 1               5

(2) INFORMATION FOR SEQ ID NO:3:

(i) SEQUENCE CHARACTERISTICS:
  (A) LENGTH: 10 amino acid
  (B) TYPE: amino acid
  (D) TOPOLOGY: linear (ii) MOLECULE TYPE:peptide (xi) SEQUENCE DESCRIPTION: SEQ ID NO:3:

Asp Arg Val Tyr Ile His Pro Phe His Leu
 1               5                   10

(2) INFORMATION FOR SEQ ID NO:4:

(i) SEQUENCE CHARACTERISTICS:
  (A) LENGTH: 8 amino acid
  (B) TYPE: amino acid
  (D) TOPOLOGY: linear (ii) MOLECULE TYPE:peptide (xi) SEQUENCE DESCRIPTION: SEQ ID NO:4:

Asp Arg Val Tyr Ile His Pro Phe
 1               5

(2) INFORMATION FOR SEQ ID NO:5:

(i) SEQUENCE CHARACTERISTICS:
  (A) LENGTH: 4 amino acid
  (B) TYPE: amino acid
  (D) TOPOLOGY: linear (ii) MOLECULE TYPE:peptide (xi) SEQUENCE DESCRIPTION: SEQ ID NO:5:

Gly Arg Gly Asp
 1

(2) INFORMATION FOR SEQ ID NO:6:

(i) SEQUENCE CHARACTERISTICS:
  (A) LENGTH: 4 amino acid
  (B) TYPE: amino acid
  (D) TOPOLOGY: linear (ii) MOLECULE TYPE:peptide ( x i ) SEQUENCE DESCRIPTION: SEQ ID NO:6:

Tyr His Arg Arg
 1

( 2 ) INFORMATION FOR SEQ ID NO:7:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:7:

Tyr Tyr His Arg Arg
 1                 5

( 2 ) INFORMATION FOR SEQ ID NO:8:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:8:

Tyr Tyr His Lys Arg
 1                 5

( 2 ) INFORMATION FOR SEQ ID NO:9:

( i ) SEQUENCE CHARACTERISTICS:
        ( A ) LENGTH: 4 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:9:

Glu His Lys Arg
 1

( 2 ) INFORMATION FOR SEQ ID NO:10:

( i ) SEQUENCE CHARACTERISTICS:
        ( A ) LENGTH: 4 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:10:

Tyr Tyr His His
 1

( 2 ) INFORMATION FOR SEQ ID NO:11:

( i ) SEQUENCE CHARACTERISTICS:
        ( A ) LENGTH: 6 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:11:

Asp Glu Tyr His Lys Arg
 1                 5

( 2 ) INFORMATION FOR SEQ ID NO:12:

( i ) SEQUENCE CHARACTERISTICS:
        ( A ) LENGTH: 6 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:12:

Asp Asp Asp Asp Asp Arg
1                   5

( 2 ) INFORMATION FOR SEQ ID NO:13:

( i ) SEQUENCE CHARACTERISTICS:
        ( A ) LENGTH: 4 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:13:

Glu His Arg Arg
1

( 2 ) INFORMATION FOR SEQ ID NO:14:

( i ) SEQUENCE CHARACTERISTICS:
        ( A ) LENGTH: 6 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:14:

Asp Glu His Arg Arg Arg
1                   5

( 2 ) INFORMATION FOR SEQ ID NO:15:

( i ) SEQUENCE CHARACTERISTICS:
        ( A ) LENGTH: 6 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:15:

Glu His His His Lys Arg
1                   5

( 2 ) INFORMATION FOR SEQ ID NO:16:

( i ) SEQUENCE CHARACTERISTICS:
        ( A ) LENGTH: 6 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:16:

His His His His His His
1                   5

( 2 ) INFORMATION FOR SEQ ID NO:17:

( i ) SEQUENCE CHARACTERISTICS:
        ( A ) LENGTH: 4 amino acid (B) TYPE: amino acid
(D) TOPOLOGY: linear (i i) MOLECULE TYPE:peptide (x i) SEQUENCE DESCRIPTION: SEQ ID NO:17:

Asp His His Arg
 1

(2) INFORMATION FOR SEQ ID NO:18:

(i) SEQUENCE CHARACTERISTICS:
(A) LENGTH: 8 amino acid
(B) TYPE: amino acid
(D) TOPOLOGY: linear (i i) MOLECULE TYPE:peptide (x i) SEQUENCE DESCRIPTION: SEQ ID NO:18:

Asp Asp Glu His His His Lys Arg
 1               5

(2) INFORMATION FOR SEQ ID NO:19:

(i) SEQUENCE CHARACTERISTICS:
(A) LENGTH: 12 amino acid
(B) TYPE: amino acid
(D) TOPOLOGY: linear (i i) MOLECULE TYPE:peptide (x i) SEQUENCE DESCRIPTION: SEQ ID NO:19:

Asp Asp Asp Asp Glu Glu His Arg Arg Arg Arg Arg
 1               5                   1 0

(2) INFORMATION FOR SEQ ID NO:20:

(i) SEQUENCE CHARACTERISTICS:
(A) LENGTH: 8 amino acid
(B) TYPE: amino acid
(D) TOPOLOGY: linear (i i) MOLECULE TYPE:peptide (x i) SEQUENCE DESCRIPTION: SEQ ID NO:20:

Asp Asp Asp Glu His His Arg Arg
 1               5

(2) INFORMATION FOR SEQ ID NO:21:

(i) SEQUENCE CHARACTERISTICS:
(A) LENGTH: 10 amino acid
(B) TYPE: amino acid
(D) TOPOLOGY: linear (i i) MOLECULE TYPE:peptide (x i) SEQUENCE DESCRIPTION: SEQ ID NO:21:

Asp Asp Asp Glu Glu Glu His Arg Arg Arg
 1               5                   1 0

(2) INFORMATION FOR SEQ ID NO:22:

(i) SEQUENCE CHARACTERISTICS:
(A) LENGTH: 7 amino acid
(B) TYPE: amino acid
(D) TOPOLOGY: linear (i i) MOLECULE TYPE:peptide ( x i ) SEQUENCE DESCRIPTION: SEQ ID NO:22:

Arg Arg Val Tyr Ile His Lys
1                       5

( 2 ) INFORMATION FOR SEQ ID NO:23:

( i ) SEQUENCE CHARACTERISTICS:
    ( A ) LENGTH: 5 amino acid
    ( B ) TYPE: amino acid
    ( D ) TOPOLOGY: linear ( i i ) MOLECULE TYPE:peptide ( x i ) SEQUENCE DESCRIPTION: SEQ ID NO:23:

Arg Arg Lys His Tyr
1               5

( 2 ) INFORMATION FOR SEQ ID NO:24:

( i ) SEQUENCE CHARACTERISTICS:
    ( A ) LENGTH: 4 amino acid
    ( B ) TYPE: amino acid
    ( D ) TOPOLOGY: linear ( i i ) MOLECULE TYPE:peptide ( x i ) SEQUENCE DESCRIPTION: SEQ ID NO:24:

Arg Arg His Tyr
1

( 2 ) INFORMATION FOR SEQ ID NO:25:

( i ) SEQUENCE CHARACTERISTICS:
    ( A ) LENGTH: 4 amino acid
    ( B ) TYPE: amino acid
    ( D ) TOPOLOGY: linear ( i i ) MOLECULE TYPE:peptide ( x i ) SEQUENCE DESCRIPTION: SEQ ID NO:25:

Arg Lys His Tyr
1

( 2 ) INFORMATION FOR SEQ ID NO:26:

( i ) SEQUENCE CHARACTERISTICS:
    ( A ) LENGTH: 6 amino acid
    ( B ) TYPE: amino acid
    ( D ) TOPOLOGY: linear ( i i ) MOLECULE TYPE:peptide ( x i ) SEQUENCE DESCRIPTION: SEQ ID NO:26:

Arg Arg Val Tyr Ile Tyr
1                   5

( 2 ) INFORMATION FOR SEQ ID NO:27:

( i ) SEQUENCE CHARACTERISTICS:
    ( A ) LENGTH: 6 amino acid
    ( B ) TYPE: amino acid
    ( D ) TOPOLOGY: linear ( i i ) MOLECULE TYPE:peptide ( x i ) SEQUENCE DESCRIPTION: SEQ ID NO:27:

Arg Asp Asp Asp Asp Asp
1                   5

( 2 ) INFORMATION FOR SEQ ID NO:28:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:28:

Tyr His Lys Arg Arg
1                 5

( 2 ) INFORMATION FOR SEQ ID NO:29:

( i ) SEQUENCE CHARACTERISTICS:
        ( A ) LENGTH: 4 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:29:

Tyr His Lys Arg
1

( 2 ) INFORMATION FOR SEQ ID NO:30:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:30:

Asp Asp Asp Asp Asp
1                 5

( 2 ) INFORMATION FOR SEQ ID NO:31:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:31:

Glu His Arg Arg Arg
1                 5

( 2 ) INFORMATION FOR SEQ ID NO:32:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:32:

Tyr His Lys Arg Arg
1                 5

( 2 ) INFORMATION FOR SEQ ID NO:33:

( i ) SEQUENCE CHARACTERISTICS:
        ( A ) LENGTH: 6 amino acid (B) TYPE: amino acid
(D) TOPOLOGY: linear (ii) MOLECULE TYPE:peptide (xi) SEQUENCE DESCRIPTION: SEQ ID NO:33:

Glu His His Lys Arg Arg
 1                   5

(2) INFORMATION FOR SEQ ID NO:34:

(i) SEQUENCE CHARACTERISTICS:
    (A) LENGTH: 9 amino acid
    (B) TYPE: amino acid
    (D) TOPOLOGY: linear (ii) MOLECULE TYPE:peptide (xi) SEQUENCE DESCRIPTION: SEQ ID NO:34:

Glu Tyr Tyr His His Lys Arg Arg Arg
 1                   5

(2) INFORMATION FOR SEQ ID NO:35:

(i) SEQUENCE CHARACTERISTICS:
    (A) LENGTH: 6 amino acid
    (B) TYPE: amino acid
    (D) TOPOLOGY: linear (ii) MOLECULE TYPE:peptide (xi) SEQUENCE DESCRIPTION: SEQ ID NO:35:

Glu His His Lys Lys Arg
 1                   5

(2) INFORMATION FOR SEQ ID NO:36:

(i) SEQUENCE CHARACTERISTICS:
    (A) LENGTH: 6 amino acid
    (B) TYPE: amino acid
    (D) TOPOLOGY: linear (ii) MOLECULE TYPE:peptide (xi) SEQUENCE DESCRIPTION: SEQ ID NO:36:

Asp Tyr His Lys Arg Arg
 1                   5

(2) INFORMATION FOR SEQ ID NO:37:

(i) SEQUENCE CHARACTERISTICS:
    (A) LENGTH: 8 amino acid
    (B) TYPE: amino acid
    (D) TOPOLOGY: linear (ii) MOLECULE TYPE:peptide (xi) SEQUENCE DESCRIPTION: SEQ ID NO:37:

Asp Glu Tyr His Lys Arg Arg Arg
 1                   5

(2) INFORMATION FOR SEQ ID NO:38:

(i) SEQUENCE CHARACTERISTICS:
    (A) LENGTH: 7 amino acid
    (B) TYPE: amino acid
    (D) TOPOLOGY: linear (ii) MOLECULE TYPE:peptide (x i) SEQUENCE DESCRIPTION: SEQ ID NO:38:

Asp Tyr Tyr His Lys Arg Arg
 1                   5

(2) INFORMATION FOR SEQ ID NO:39:

(i) SEQUENCE CHARACTERISTICS:
        (A) LENGTH: 10 amino acid
        (B) TYPE: amino acid
        (D) TOPOLOGY: linear (i i) MOLECULE TYPE:peptide (x i) SEQUENCE DESCRIPTION: SEQ ID NO:39:

Asp Glu Tyr Tyr His His Lys Arg Arg Arg
 1                   5                  10

(2) INFORMATION FOR SEQ ID NO:40:

(i) SEQUENCE CHARACTERISTICS:
        (A) LENGTH: 5 amino acid
        (B) TYPE: amino acid
        (D) TOPOLOGY: linear (i i) MOLECULE TYPE:peptide (x i) SEQUENCE DESCRIPTION: SEQ ID NO:40:

Glu His His Arg Arg
 1               5

(2) INFORMATION FOR SEQ ID NO:41:

(i) SEQUENCE CHARACTERISTICS:
        (A) LENGTH: 12 amino acid
        (B) TYPE: amino acid
        (D) TOPOLOGY: linear (i i) MOLECULE TYPE:peptide (x i) SEQUENCE DESCRIPTION: SEQ ID NO:41:

Asp Glu Tyr Tyr Tyr His His Lys Lys Arg Arg Arg
 1                   5                  10

(2) INFORMATION FOR SEQ ID NO:42:

(i) SEQUENCE CHARACTERISTICS:
        (A) LENGTH: 5 amino acid
        (B) TYPE: amino acid
        (D) TOPOLOGY: linear (i i) MOLECULE TYPE:peptide (x i) SEQUENCE DESCRIPTION: SEQ ID NO:42:

Glu His His Lys Arg
 1               5

(2) INFORMATION FOR SEQ ID NO:43:

(i) SEQUENCE CHARACTERISTICS:
        (A) LENGTH: 8 amino acid
        (B) TYPE: amino acid
        (D) TOPOLOGY: linear (i i) MOLECULE TYPE:peptide (x i) SEQUENCE DESCRIPTION: SEQ ID NO:43:

Asp Glu Tyr His His Arg Arg Arg
 1                   5

( 2 ) INFORMATION FOR SEQ ID NO:44:

( i ) SEQUENCE CHARACTERISTICS:
        ( A ) LENGTH: 6 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:44:

Tyr Tyr His His His Arg
1               5

( 2 ) INFORMATION FOR SEQ ID NO:45:

( i ) SEQUENCE CHARACTERISTICS:
        ( A ) LENGTH: 7 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:45:

Asp Glu Tyr His Arg Arg Arg
1               5

( 2 ) INFORMATION FOR SEQ ID NO:46:

( i ) SEQUENCE CHARACTERISTICS:
        ( A ) LENGTH: 7 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:46:

Tyr Tyr Tyr His His His Arg
1               5

( 2 ) INFORMATION FOR SEQ ID NO:47:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:47:

Tyr Tyr His His Arg
1               5

( 2 ) INFORMATION FOR SEQ ID NO:48:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:48:

Glu Tyr His Lys Arg
1               5

( 2 ) INFORMATION FOR SEQ ID NO:49:

( i ) SEQUENCE CHARACTERISTICS:
        ( A ) LENGTH: 7 amino acid (B) TYPE: amino acid
            (D) TOPOLOGY: linear (ii) MOLECULE TYPE:peptide (xi) SEQUENCE DESCRIPTION: SEQ ID NO:49:

Asp Asp Tyr His Lys Arg Arg
1               5

(2) INFORMATION FOR SEQ ID NO:50:

(i) SEQUENCE CHARACTERISTICS:
            (A) LENGTH: 5 amino acid
            (B) TYPE: amino acid
            (D) TOPOLOGY: linear (ii) MOLECULE TYPE:peptide (xi) SEQUENCE DESCRIPTION: SEQ ID NO:50:

Asp Tyr His Lys Arg
1               5

(2) INFORMATION FOR SEQ ID NO:51:

(i) SEQUENCE CHARACTERISTICS:
            (A) LENGTH: 6 amino acid
            (B) TYPE: amino acid
            (D) TOPOLOGY: linear (ii) MOLECULE TYPE:peptide (xi) SEQUENCE DESCRIPTION: SEQ ID NO:51:

Tyr Tyr Tyr His His Arg
1               5

(2) INFORMATION FOR SEQ ID NO:52:

(i) SEQUENCE CHARACTERISTICS:
            (A) LENGTH: 4 amino acid
            (B) TYPE: amino acid
            (D) TOPOLOGY: linear (ii) MOLECULE TYPE:peptide (xi) SEQUENCE DESCRIPTION: SEQ ID NO:52:

Tyr Tyr His Arg
1

(2) INFORMATION FOR SEQ ID NO:53:

(i) SEQUENCE CHARACTERISTICS:
            (A) LENGTH: 5 amino acid
            (B) TYPE: amino acid
            (D) TOPOLOGY: linear (ii) MOLECULE TYPE:peptide (xi) SEQUENCE DESCRIPTION: SEQ ID NO:53:

Tyr Tyr His Lys Arg
1               5

(2) INFORMATION FOR SEQ ID NO:54:

(i) SEQUENCE CHARACTERISTICS:
            (A) LENGTH: 5 amino acid
            (B) TYPE: amino acid
            (D) TOPOLOGY: linear (ii) MOLECULE TYPE:peptide ( x i ) SEQUENCE DESCRIPTION: SEQ ID NO:54:

Tyr Tyr Tyr His Arg
1               5

( 2 ) INFORMATION FOR SEQ ID NO:55:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:55:

His His His His His
1               5

( 2 ) INFORMATION FOR SEQ ID NO:56:

( i ) SEQUENCE CHARACTERISTICS:
        ( A ) LENGTH: 6 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:56:

Asp His His His His Arg
1               5

( 2 ) INFORMATION FOR SEQ ID NO:57:

( i ) SEQUENCE CHARACTERISTICS:
        ( A ) LENGTH: 4 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:57:

His His His His
1

( 2 ) INFORMATION FOR SEQ ID NO:58:

( i ) SEQUENCE CHARACTERISTICS:
        ( A ) LENGTH: 5 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:58:

Asp His His His Arg
1               5

( 2 ) INFORMATION FOR SEQ ID NO:59:

( i ) SEQUENCE CHARACTERISTICS:
        ( A ) LENGTH: 6 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:59:

Asp Glu His His Arg Arg
1               5

( 2 ) INFORMATION FOR SEQ ID NO:60:

( i ) SEQUENCE CHARACTERISTICS:
        ( A ) LENGTH: 9 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:60:

Asp Asp Glu Tyr His His Lys Arg Arg
1                  5

( 2 ) INFORMATION FOR SEQ ID NO:61:

( i ) SEQUENCE CHARACTERISTICS:
        ( A ) LENGTH: 4 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:61:

Tyr Tyr Tyr Arg
1

( 2 ) INFORMATION FOR SEQ ID NO:62:

( i ) SEQUENCE CHARACTERISTICS:
        ( A ) LENGTH: 8 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:62:

Asp Asp Glu Tyr His Lys Arg Arg
1                5

( 2 ) INFORMATION FOR SEQ ID NO:63:

( i ) SEQUENCE CHARACTERISTICS:
        ( A ) LENGTH: 8 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:63:

Asp Asp Asp Glu Lys Arg Arg Arg
1                5

( 2 ) INFORMATION FOR SEQ ID NO:64:

( i ) SEQUENCE CHARACTERISTICS:
        ( A ) LENGTH: 8 amino acid
        ( B ) TYPE: amino acid
        ( D ) TOPOLOGY: linear ( i i ) MOLECULE TYPE:peptide ( x i ) SEQUENCE DESCRIPTION: SEQ ID NO:64:

Asp Asp Asp Asp His His Arg Arg
1                5

( 2 ) INFORMATION FOR SEQ ID NO:65:

( i ) SEQUENCE CHARACTERISTICS:
        ( A ) LENGTH: 4 amino acid

-continued (B) TYPE: amino acid
(D) TOPOLOGY: linear (i i) MOLECULE TYPE:peptide (x i) SEQUENCE DESCRIPTION: SEQ ID NO:65:

Asp Glu Arg Arg
1

(2) INFORMATION FOR SEQ ID NO:66:

(i) SEQUENCE CHARACTERISTICS:
(A) LENGTH: 5 amino acid
(B) TYPE: amino acid
(D) TOPOLOGY: linear (i i) MOLECULE TYPE:peptide (x i) SEQUENCE DESCRIPTION: SEQ ID NO:66:

Asp Glu Glu Lys Arg
1

(2) INFORMATION FOR SEQ ID NO:67:

(i) SEQUENCE CHARACTERISTICS:
(A) LENGTH: 4 amino acid
(B) TYPE: amino acid
(D) TOPOLOGY: linear (i i) MOLECULE TYPE:peptide (x i) SEQUENCE DESCRIPTION: SEQ ID NO:67:

Asp Asp Glu Arg
1

(2) INFORMATION FOR SEQ ID NO:68:

(i) SEQUENCE CHARACTERISTICS:
(A) LENGTH: 4 amino acid
(B) TYPE: amino acid
(D) TOPOLOGY: linear (i i) MOLECULE TYPE:peptide (x i) SEQUENCE DESCRIPTION: SEQ ID NO:68:

Asp Asp Asp Arg
1

(2) INFORMATION FOR SEQ ID NO:69:

(i) SEQUENCE CHARACTERISTICS:
(A) LENGTH: 5 amino acid
(B) TYPE: amino acid
(D) TOPOLOGY: linear (i i) MOLECULE TYPE:peptide (x i) SEQUENCE DESCRIPTION: SEQ ID NO:69:

Asp Asp Asp Asp Arg
1               5

ISOELECTRIC POINT MARKERS FOR ISOELECTRIC FOCUSING WITH FLUORESCENCE DETECTION

BACKGROUND OF THE INVENTION

1. Field of the Invention

The present invention relates to isoelectric point markers for isoelectric focusing with fluorescence detection.

2. Related Background Art

Since Picton, H. and Linder, S. E. observed in 1892 that when an electric field is supplied as particles with charges on the surfaces are suspended in an electrolyte solution, the particles migrate toward the opposite poles to the charges of the respective particles, the phenomenon, electrophoresis has been used as means of separation and analysis. After Tiselius has completed his apparatus in 1937, fields of applications have been expanding rapidly heretofore.

Ordinary electrophoresis utilizes differences of net charge states at a certain specific pH, whereas after Vesterberg, 0. and Svensson, H. developed carrier ampholytes as an amphoteric electrolyte in 1966, the isoelectric focusing has been established utilizing a phenomenon that each ampholyte electrolyte has the effective net charge of zero at a certain pH so as to stop migrating.

Here, the value of pH where the effective charge becomes zero is called as an isoelectric point of that substance. In the isoelectric focusing method, a substance stops as concentrated at a position equal to the isoelectric point on a pH gradient formed in a focusing carrier.

Since substances are separated as concentrated in a focusing manner as described, it may provide a separation or analytical method with much higher sensitivity in an electrophoresis.

Further developed recently was a capillary isoelectric focusing in which electrophoresis was effected in a fine tube (capillary) made of a fused silica and having the inner diameter 5 to 100 μm and the length of 30 to 100 cm. Since the capillary isoelectric focusing has a high resolution with a small amount of sample, it has been applied to not only separation and analysis of proteins, but also separation and analysis of inorganic ions, low-molecular weight compounds, and nucleic acids.

There are further attempts to quantify concentrations of separated components in a sample by a detector set at one end of the capillary tube.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
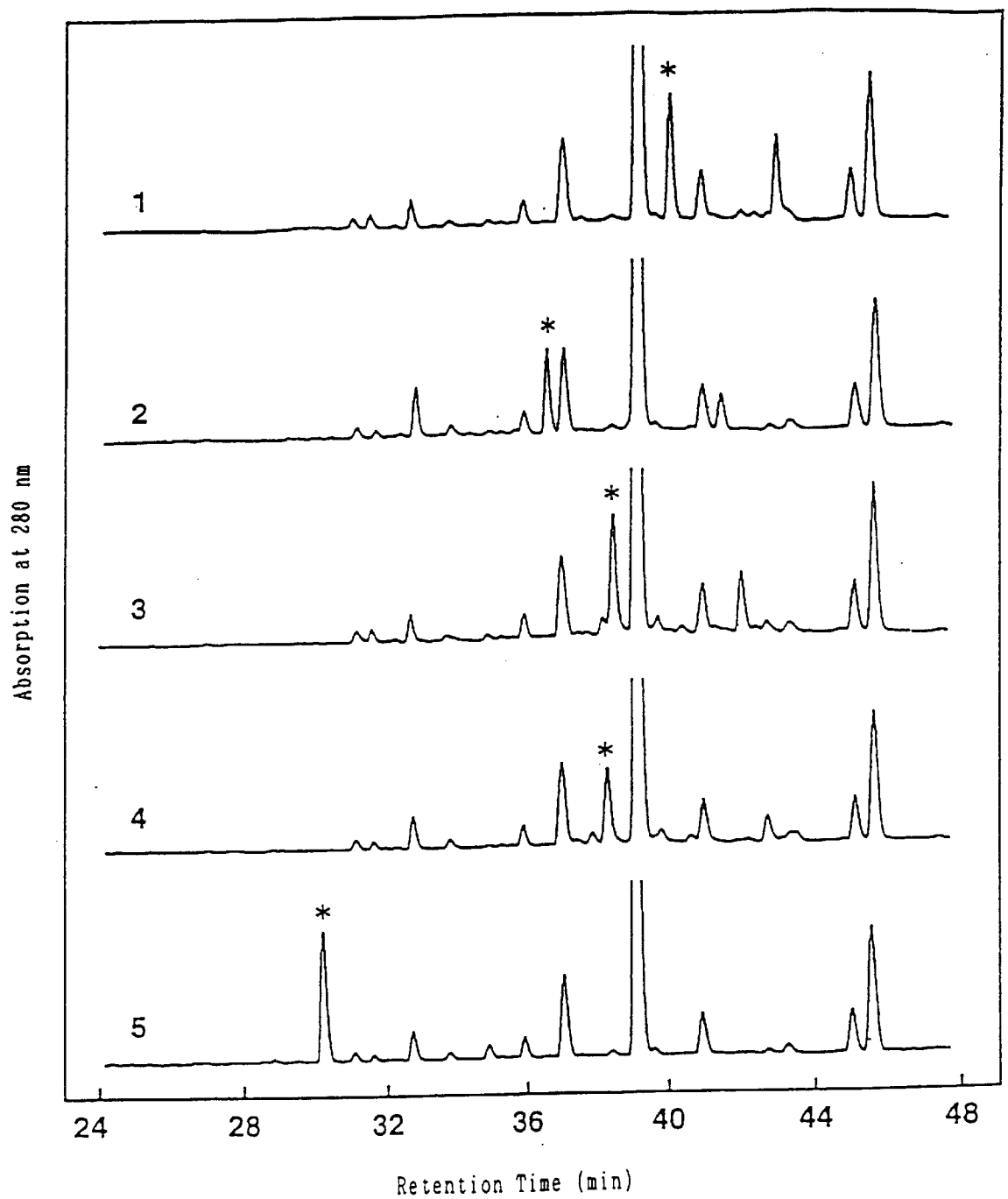
FIG. 1 is a drawing to show chromatograms and identified specific peaks (*) of five types of fluorescence-labeled peptides(1–5) according to the present invention, as separated by high performance liquid chromatography.
Figure 2:
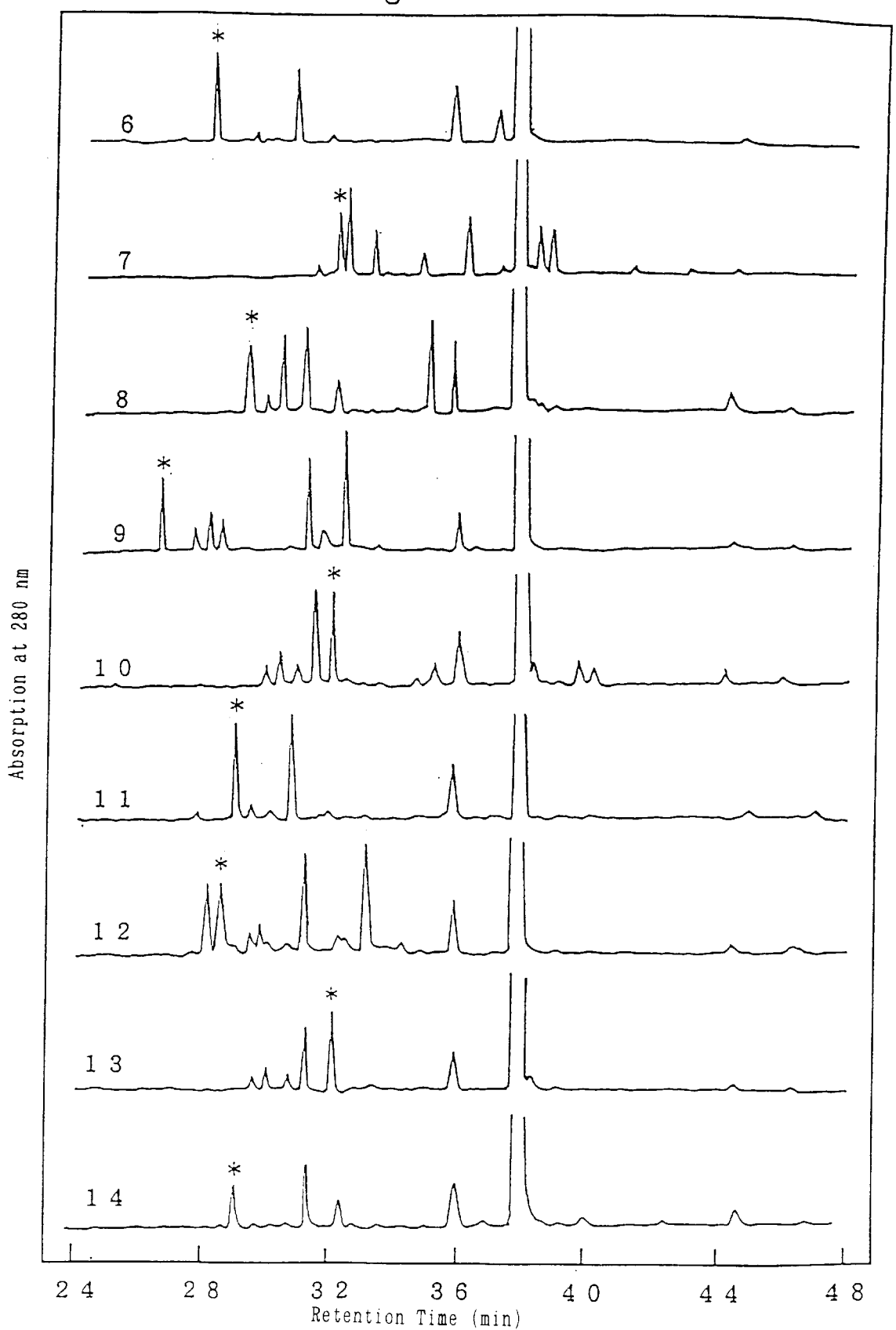
FIG. 2 is a drawing to show chromatograms and identified specific peaks (*) of nine types of fluorescence-labeled peptides(6–14) according to the present invention, as separated by high performance liquid chromatography.
Figure 3:
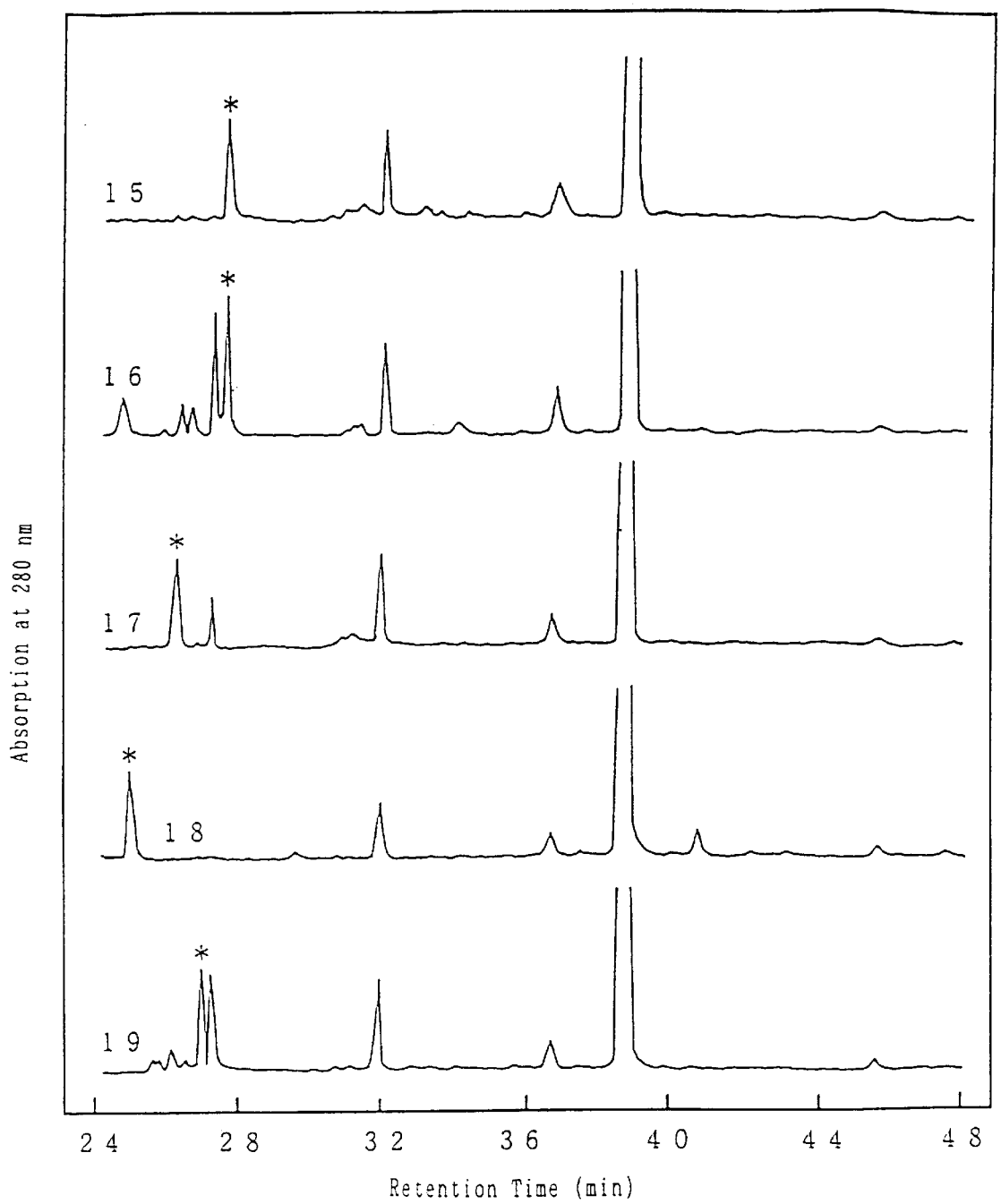
FIG. 3 is a drawing to show chromatograms and identified specific peaks (*) of five types of fluorescence-labeled peptides(15–19) according to the present invention, as separated by high performance liquid chromatography.
Figure 4:
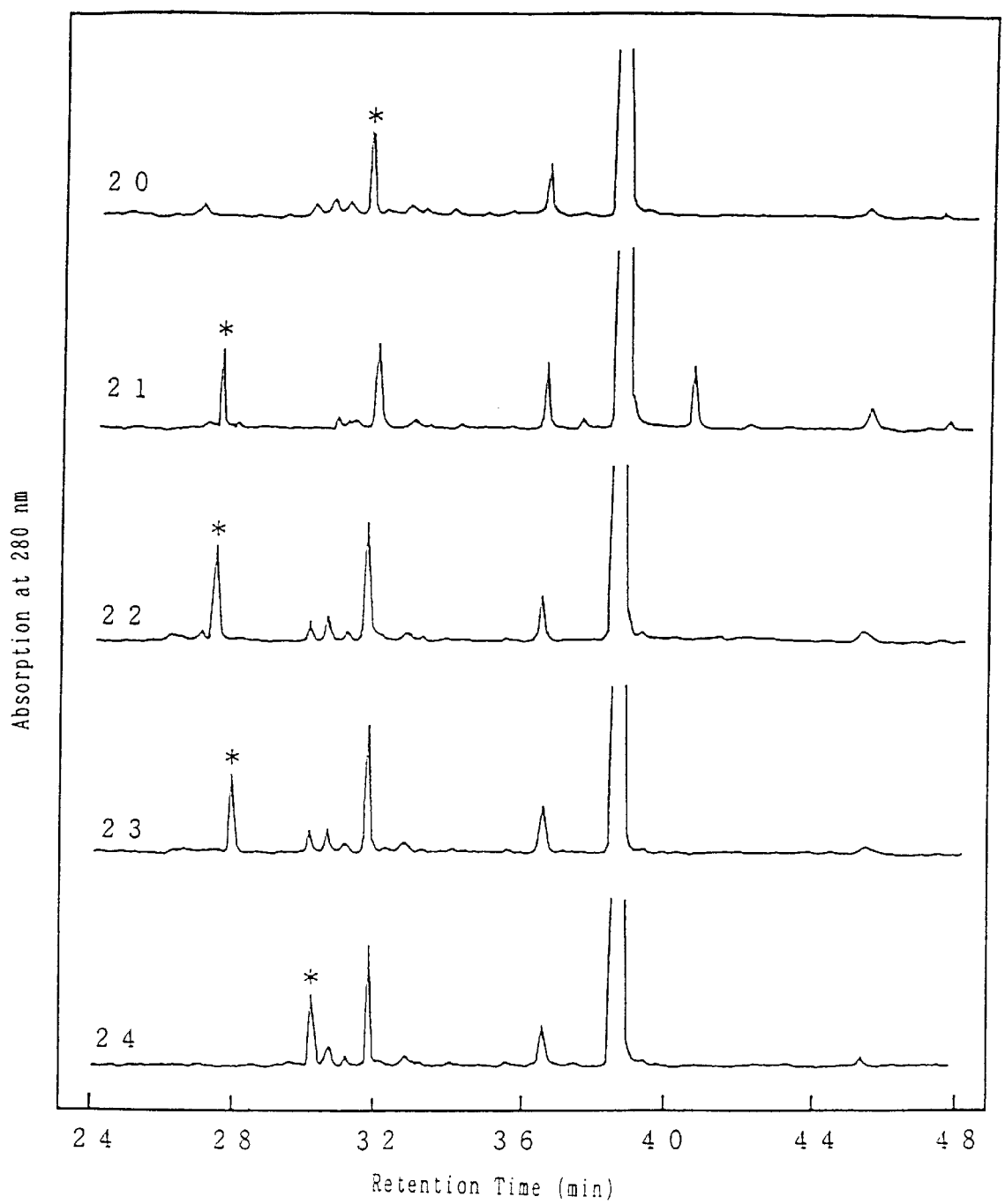
FIG. 4 is a drawing to show chromatograms and identified specific peaks (*) of five types of fluorescence-labeled peptides(20–24) according to the present invention, as separated by high performance liquid chromatography.

In the drawings, reference numerals denote the following peptides.

1: des-asparaginic acid$^1$-angiotensin I (arginine-valine-tyrosine-isoleucine-histidine-proline -phenylalanine-histidine-leucine, Arg-Val-Tyr-Ile-HisPro-Phe-His-Leu) (SEQ ID NO:1);

2: [asparagine$^1$-valine$^5$]-angiotensin II (asparagine-arginine-valine-tyrosine-valine-histidine-proline-phenylalanine, Asn-Arg-Val-Tyr-Val-His-Pro-Phe) (SEQ ID NO:2);

3: angiotensin I (asparaginic acid-arginine-valine-tyrosine-isoleucine-histidine-proline-phenylalanine-histidine-leucine, Asp-Arg-Val-Tyr-Ile-His-Pro-Phe-His-Leu) (SEQ ID NO:3);

4: angiotensin II (asparaginic acid-arginine-valine-tyrosine-isoleucine-histidine-proline-phenylalanine, Asp-Arg-Val-Tyr-Ile-His-Pro-Phe) (SEQ ID NO:4);

5: fibronectin fragment (glycine-arginine-glycine-asparaginic acid, Gly-Arg-Gly-Asp) (SEQ ID NO:5);

6: tyrosine-histidine-arginine-arginine (Tyr-His-Arg-Arg) (SEQ ID NO:6);

7: tyrosine-tyrosine-histidine-arginine-arginine (Tyr-Tyr-His-Arg-Arg) (SEQ ID NO:7);

8: tyrosine-tyrosine-histidine-lysine-arginine (Tyr-Tyr-His-Lys-Arg) (SEQ ID NO:8);

9: glutamic acid-histidine-lysine-arginine (Glu-His-Lys-Arg) (SEQ ID NO:9);

10: tyrosine-tyrosine-histidine-histidine (Tyr-Tyr-His-His) (SEQ ID NO:10);

11: tyrosine-histidine-histidine (Tyr-His-His);

12: asparaginic acid-glutamic acid-tyrosine-histidine-lysine-arginine (Asp-Glu-Tyr-His-Lys-Arg) (SEQ ID NO:11);

13: tyrosine-histidine (Tyr-His);

14: asparaginic acid-asparaginic acid-asparaginic acid-asparaginic acid-asparaginic acid-arginine (Asp-Asp-Asp-Asp-Asp-Arg) (SEQ ID NO:12).

15: glycine-histidine-arginine-arginine (Glu-His-Arg-Arg) (SEQ ID NO:13).

16: asparaginic acid-glutaminic acid-histidine-arginine-arginine-arginine (Asp-Glu-His-Arg-Arg-Arg) (SEQ ID NO:14).

17: glutaminic acid-histidine-histidine-histidine-lysine-arginine (Glu-His-His-His-Lys-Arg) (SEQ ID NO:15)

18: histidine-histidine-histidine-histidine-histidine (His-His-His-His-His) (SEQ ID NO:16).

19: asparagic acid-histidine-histidine-arginine (Asp-His-His-Arg) (SEQ ID NO:17).

20: asparagic acid-asparagic acid-glutamic acid-histidine-histidine-histidine-lysine-arginine (Asp-Asp-Glu-His-His-His-Lys-Arg) (SEQ ID NO:18).

21: asparagic acid-asparagic acid-asparagic acid-asparagic acid-glutamic acid-glutamic acid-histidine-arginine-arginine-arginine-arginine-arginine (Asp-Asp-Asp-Asp-Glu-Glu-His-Arg-Arg-Arg-Arg-Arg) (SEQ ID NO:19).

22: asparagic acid-asparagic acid-asparagic acid-glutamic acid-histidine-arginine-arginine (Asp-Asp-Asp-Glu-His-His-Arg-Arg) (SEQ ID NO:18).

23: asparagic acid-asparagic acid-asparagic acid-glutamic acid-glutamic acid-glutamic acid-histidinearginine-arginine-arginine (Asp-Asp-Asp-Glu-Glu-Glu-His-Arg-Arg-Arg) (SEQ ID NO:19)

24: asparagic acid-glutamic acid-arginine (Asp-Glu-Arg).

SUMMARY OF THE INVENTION

One of conventional detection for analytical method is to focus mainly ultraviolet light or visible light on a sample and to detect amounts of components in the sample by changes of light absorption (ultraviolet or visible light detection).

Such detection method is, however, difficult to use for the capillary isoelectric focusing, because the inner diameter of the capillary tube is almost equal to optical path length.

Another detection method with high sensitivity uses fluorescence-labeled sample with a fluorescence labeling material such as dyes. Excitation light is focused on to separated components in the sample, and emitted fluorescence is detected to quantify concentrations of the components (fluorescence detection).

For labeling a sample such as a mixture of proteins, fluorescence materials(dyes) is usually reacted with the sample to form a chemical bond between an amino group in sample protein and the fluorescence dye. For example, fluorescein isothiocyanate (FITC) and tetramethylrhodamine isothiocyanate (TRITC), etc. are known as fluorescence dyes to be bonded with an amino group (Motonori ONO, Yuichi KANEOKA, Fumio SAKIYAMA, and Hiroshi MAEDA, Chemical Modification of Proteins (II), Gakkai Shuppan Center, 1981).

The fluorescence detection can be adequately used in the capillary isoelectric focusing to quantify the amounts of separated components in a sample. Therefore, the fluorescence detection combined with a capillary isoelectric focusing system may be a potential analytical system of a mixture of proteins because of dual advantages of high resolution and high detection sensitivity.

The pH gradient formed in the focusing carrier, however, should be known precisely in isoelectric focusing, because an isoelectric point (pI) is determined based on a stop position of a sample component separated in the focusing carrier. Therefore, pI markers as standards are required to estimate formed pH gradient.

For electrophoresis or isoelectric focusing with fluorescence detection it is extremely difficult to use conventional protein pI markers as pI standards, which have known pI's (for example, trypsinogen (pI=9.30), lentilectin (pI=7.80, 8.00, 8.20), human hemoglobin C (pI=7.50), human hemoglobin A (pI=7.10), equine myoglobin (pI=7.00), human carbonic anhydrase (pI=6.50), bovine carbonic anhydrase (pI=6.00), β-lactoglobulin B (pI=5.10), phycocyanin (pI=4.65), amyloglucosidase (pI=3.50), etc.), since these proteins per se can emit only very weak fluorescence. Such proteins need to increase fluorescence intensity by labeling with an appropriate fluorescence materials However, the pI's of the proteins are in general dependent on types of amino acids composing the proteins and N-terminal amino groups, (Chemistry of Proteins (I), Second Series of Lectures on Biochemical Experiments No. 2, the Japanese Biochemical Society, 1987). Then, the isoelectric points, pI's of the proteins per se would be changed by any chemical modification on the N-terminal amino groups of such proteins with the fluorescence label.

Further, a protein includes amino acids reactive to a fluorescent labeling material, numbers and positions of fluorescence labeling materials bonded thereto are unspecified. Consequently, the modification provides a mixture of proteins labeled at different positions to give different pI's (Flatmark, T. and Vesterberg, O., Acta Chem. Scand., 20, 1497–1503, 1966). Therefore, it is difficult to determine precise pH regions formed in the focusing carrier by such labeled proteins mixture described above.

Further, the three-dimensional structure of protein may be altered by those labeling with the fluorescence material (Williamson, A. R., Kreth and H. W., Ann. N. Y. Acad. Sci., 209, 211–224, 1973), which may deteriorate stability of protein per se.

This would be a problem in respect of storage stability of the proteins as pI markers.

As discussed above, the isoelectric focusing with fluorescence detection cannot use such labeled proteins with fluorescence materials as pI markers.

The present inventors have extensively and intensively been studying to solve the above problems, and found out that fluorescence-labeled oligopeptides demonstrated single and peculiar pI's and covered a wide range of pI's ,and they were also excellent in storage stability, thus achieving the present invention.

The present invention concerns markers for isoelectric focusing with fluorescence detection obtained by selecting appropriate oligopeptides and further labeling them with a suitable fluorescence material in order to accurately clarify pH regions formed in the focusing carrier in isoelectric focusing, which are characterized by demonstrating uniform pI's and high storage stability.

Namely, the present invention concerns a marker for isoelectric focusing with fluorescence detection, which is an oligopeptide comprising a fluorescence dye.

Further, the present invention concerns the marker for isoelectric focusing with fluorescence detection, which is an oligopeptide obtained by bonding the fluorescence dye materials to an N-terminal amino group of the oligopeptide.

Further, the present invention concerns the marker for isoelectric focusing with fluorescence detection, wherein the bonding is one selected from the group at least comprising amide, thioamide, sulfonamide, urea, thiourea, and urethane bonding groups.

Further, the present invention concerns the marker for isoelectric focusing with fluorescence detection, wherein the oligopeptide comprises at least $n_j$ amino acids, each having a group which is to release a proton, thereby resulting in having a negative charge, wherein the group to release the proton thereby to have the negative charge has an acid dissociation constant of $K_j$, and/or $n_i$ amino acids, each having a group which is to receive a proton, thereby resulting in having a positive charge, wherein the group to receive the proton thereby to have the positive charge has an acid dissociation constant of $K_i$, and wherein, defining that $Z=\Sigma_i(n_i/(1+K_i/[H^+]))-\Sigma_j(n_j/(1+[H^+]/K_j))$ and that pI is $-\log([H^+])$ when $|Z|<0.01$ is satisfied, $3<pI<11$.

Further, the present invention concerns the marker for isoelectric focusing with fluorescence detection, wherein the oligopeptide is angiotensin or a related compound thereof.

Further the present invention concerns the marker for isoelectric focusing with fluorescence detection, wherein the oligopeptide is at least one oligopeptide selected from the group at least comprising Arg-Arg-Val-Tyr-Ile-His-Lys (SEQ ID NO:22), Arg-Arg-Lys-His-Tyr (SEQ ID NO:23), Arg-Arg-His-Tyr (SEQ ID NO:24), Arg-Lys-His-Tyr (SEQ ID NO:25), Arg-Arg-Val-Tyr-Ile-Tyr (SEQ ID NO:26), Arg-Val-Tyr-Ile-His-Pro-Phe-His-Leu (SEQ ID NO:1), Asn-Arg-Val-Tyr-Val-His-Pro-Phe (SEQ ID NO:2), Asp-Arg-Val-Tyr-Ile-His-Pro-Phe-His-Leu (SEQ ID NO:3), Asp-Arg-Val-Tyr-Ile-His-Pro-Phe (SEQ ID NO:4), Gly-Arg-Gly-Asp (SEQ ID NO:5), and Arg-Asp-Asp-Asp-Asp-Asp (SEQ ID NO:27).

Further, the present invention concerns the marker for isoelectric focusing with fluorescence detection, wherein the fluorescence dye is one selected from the group comprising rhodamine, fluorescein, cyanine, indocyanine, indocarbocyanine, pyronine, lucifer yellow, quinacrine, squarillium, coumarin, fluoroanthranilmaleimide, and anthracene.

Further, the present invention concerns the marker for isoelectric focusing with fluorescence detection, wherein the isoelectric focusing is a capillary isoelectric focusing with fluorescence detection method.

Further, the present invention concerns the marker for isoelectric focusing with fluorescence detection, wherein the oligopeptide is at least one oligopeptide selected from the group at least comprising Tyr-His-Lys-Arg-Arg (SEQ ID NO:28), Tyr-His-Lys-Arg (SEQ ID NO:29), Asp-His-His-Arg (SEQ ID NO:17), Asp-His-Arg, Arg-Arg-Val-Tyr-Ile-His-Lys (SEQ ID NO:22), Arg-Arg-Lys-His-Tyr (SEQ ID NO:23), Arg-Arg-His-Tyr (SEQ ID NO:24), Arg-Lys-His-Tyr (SEQ ID NO:25), Arg-Arg-Val-Tyr-Ile-Tyr (SEQ ID NO:26), Arg-Val-Tyr-Ile-His-Pro-Phe-His-Leu (SEQ ID NO:1), Asn-Arg-Val-Tyr-Val-His-Pro-Phe (SEQ ID NO:2), Asp-Arg-Val-Tyr-Ile-His-Pro-Phe-His-Leu (SEQ ID NO:3), Asp-Arg-Val-Tyr-Ile-His-Pro-Phe (SEQ ID NO:4), Gly-Arg-Gly-Asp (SEQ ID NO:5), Arg-Asp-Asp-Asp-Asp-Asp (SEQ ID NO:27), Tyr-His-Arg-Arg (SEQ ID NO:28), Tyr-Tyr-His-Arg-Arg (SEQ ID NO:7), Tyr-Tyr-His-Lys-Arg (SEQ ID NO:8), Glu-His-Lys-Arg (SEQ ID NO:9), Tyr-Tyr-His-His (SEQ ID NO:10), Tyr-His-His, Asp-Glu-Tyr-His-Lys-Arg (SEQ (ID NO:11), Tyr-His, Arg (SEQ ID NO:12), Glu-His-Arg-Arg (SEQ ID NO:13), Asp-Glu-His-Arg-Arg (SEQ ID NO:14), Glu-His-His-His-Lys-Arg (SEQ ID NO:15), His-His-His-His-His-His (SEQ ID NO:16), Asp-His-His-Arg (SEQ ID NO:17), Asp-Asp-Glu-His-His-His-Lys-Arg (SEQ ID NO:18), Asp-Asp-Asp-Asp-Glu-Glu-His-Arg-Arg-Arg-Arg-Arg (SEQ ID NO:19), Asp-Asp-Asp-Glu-His-His-Arg-Arg (SEQ ID NO:20), Asp-Asp-Asp-Glu-Glu-Glu-His-Arg-Arg-Arg (SEQ ID NO:21), and Asp-Glu-Arg.

Further, the present invention concerns the marker for isoelectric focusing with fluorescence detection, wherein said oligopeptide at least comprises Arg-Val-Tyr-Ile-His-Pro-Phe-His-Leu (SEQ ID NO:1), Asn-Arg-Val-Tyr-Val-His-Pro-Phe SEQ ID NO:2), Asp-Arg-Val-Tyr-Ile-His-Pro-Phe-His-Leu (SEQ ID NO:3), Asp-Arg-Val-Tyr-Ile-His-Pro-Phe (SEQ ID NO:4), Gly-Arg-Gly-Asp (SEQ ID NO:5), Tyr-His-Arg-Arg (SEQ ID NO:7), Tyr-Tyr-His-Arg-Arg (SEQ ID NO:8), Tyr-Tyr-His-Lys-Arg, Glu-His-Lys-Arg (SEQ ID NO:9, Tyr-Tyr-His-His (SEQ ID NO:10), Tyr-His-His, Asp-Glu-Tyr-His-Lys-Arg (SEQ ID NO:11), Tyr-His, Asp-Asp-Asp-Asp-Asp-Arg (SEQ ID NO:12), Glu-His-Arg-Arg (SEQ ID NO:13), Asp-Glu-His-Arg-Arg-Arg (SEQ ID NO:14), Glu-His-His-His-Lys-Arg (SEQ ID NO:15), His-His-His-His-His-His, (SEQ ID NO:16) Asp-His-His-Arg (SEQ ID NO:17), Asp-Asp-Glu-His-His-His-Lys-Arg (SEQ ID NO:18), Asp-Asp-Asp-Asp-Glu-Glu-His-Arg-Arg-Arg-Arg-Arg (SEQ ID NO:19), Asp-Asp-Asp-Glu-His-His-Arg-Arg (SEQ ID NO:20), Asp-Asp-Asp-Glu-Glu-Glu-His-Arg-Arg-Arg (SEQ ID NO:21), and Asp-Glu-Arg.

DETAILED DESCRIPTION OF THE PREFERRED EMBODIMENTS

Embodiments of the present invention will be explained in detail.

(Oligopeptides)

The present invention employs oligopeptides in particular out of various ampholytes applicable as markers. In the isoelectric focusing, samples to be analyzed are proteins including oligopeptide, or other type of materials which contain peptides as a component. Therefore, use of oligopeptides comprised of dissociable groups similar to proteins is preferred in order to check pI values of such samples.

However, if an oligopeptide should include too many amino acids, there would exist a plurality of reaction sites for labeling with fluorescence dye, which would provide a mixture of labeled products depending upon reaction conditions. In this case a marker thus obtained would not demonstrate a single and narrow peak, which is not preferred for pI markers for isoelectric focusing with fluorescence detection.

In the present invention there is no specific limitation on the number of amino acids for an oligopeptide, and the present invention may employ any oligopeptide having a sufficient number of amino groups to achieve an aimed pI accordingly.

Oligopeptides consist of various type of amino acids as amphoteric compounds have various type of acid groups and basic groups as acid- base dissociable groups, and the oligopeptides have a N-terminal amino group, and a C-terminal carboxylic acid group. For example, amino acids having an acid group include asparaginic acid, glutamic acid, tyrosine, etc., and amino acids having a basic group include lysine, arginine, histidine, etc.

Because of these acid and basic dissociable groups, an oligopeptide shows a specific charge number at a certain pH. Accordingly, a charge number of an oligopeptide as a whole can be calculated from types and numbers of these acid and basic dissociable groups.

For example, a charge number (z) of an oligopeptide as a whole can be estimated by the following equation.

$$Z=\Sigma_i(n_i/(1+K_i/[H^+]))-\Sigma_j(n_j/(1+[H^+]/K_j))$$

The above equation gives a total charge number (Z) of an oligopeptide including $n_j$ amino acids, each having a group which is to discharge a proton, thereby resulting in having a negative charge, wherein the group to discharge a proton thereby to have a negative charge has an acid dissociation constant of $K_j$, and $n_i$ amino acids, each having a group which is to receive a proton, thereby resulting in having a positive charge, wherein the group to receive a proton thereby to have a positive charge has an acid dissociation constant of $K_i$ (Kagaku no Ryoiki, Regions of Chemistry, 36, 34–50).

Further, an isoelectric point pI of the oligopeptide is given as $-\log([H^+])=pH$ at $Z=0$ in this equation.

Therefore, it becomes possible to select amino acid necessary for an oligopeptide to demonstrate an aimed pI by utilizing this equation.

If any group including a fluorescence dye is bonded to the N-terminal amino group of an oligopeptide, basic dissociation of the N-terminal amino group becomes restrained.

For estimation pI and selecting appropriate amino acids, available pKa's of above acidic and basic dissociable groups are, for example, α-carboxylic acid (C-terminal) (3.6), β-carboxylic acid (Asp) (3.95), γ-carboxylic acid (Glu) (4.45), imidazole (His) (6.45), α-amino (N-terminal) (7.6), thiol (Cys) (8.5), phenylhydroxy (Tyr) (9.8), ε-amino (Lys) (10.2), and guanidinium group (Arg) (12.5).

For example, in the case of an oligopeptide labeled at the N-terminal, asparaginic acid or glutamic acid is selected to decrease pI, while arginine or lysine is selected to increase pI. Similarly, tyrosine or histidine may be selected in order to determine pI between them.

An example of very small pI is an oligopeptide including at least five asparaginic acids and one arginine as acidic, and basic amino acids, which demonstrates pI near 3.

Similarly, an oligopeptide including at least two arginines, one lysine, one histidine, and one tyrosine shows a pI of not less than 11.

In this manner, markers covering a desired range of pI can be obtained by suitably selecting some of various acidic, and basic amino acids.

In the present invention, a preferred range of pI is between 2 and 13 both inclusive.

In the present invention, a particularly preferred range of pI is between 3 and 11 both inclusive.

Further, the present invention requires no specific limitation for synthesis of an oligopeptide including amino acids appropriately selected. A preferably applicable peptide synthesis method is, for example, an ordinary organic synthesis (the liquid phase process, the solid phase process, etc., Nobuo IZUMIYA, Tetsuo KATO, Haruhiko AOYAGI, and Michinori WAKI, Fundamentals and Experiments of Peptide Synthesis, Maruzen, 1985), or o use an automated synthesizer.

The present invention can also suitably employ all or some of oligopeptides derived from natural products as long as they include necessary amino acid groups and reactive site for fluorescence labeling thereof.

For example, oligopeptides obtained from natural products, which the present invention can suitably employ, include angiotensin and related compounds thereof (10 to 20 amino acids), bradykinin and related compounds thereof, enkephalin and related compounds thereof, etc. (Dictionary of Biochemistry (Second Edition), Tokyo Kagaku Dojin, 1990).

Further, it is also possible to synthesize an oligopeptide having appropriate amino acid by bonding chemically necessary amino acid to one selected from the above oligopeptides derived from natural products.

(Fluorescence dye)

There is no specific limitation on the type of fluorescence applicable in the present invention, and any fluorescence dye including a generally known fluorescent pigment may be employed.

For example, the fluorescence dye may be rhodamine, fluorescein, cyanine, indocyanine, indocarbocyanine, pyronine, lucifer yellow, quinacrine, squarillium, coumarin, fluoroanthranilmaleimide, etc.

Particularly, rhodamine and cyanine pigments are preferably applicable.

A particularly preferred fluorescence dye derivative in the present invention is a 5-carboxytetramethylrhodamine fluorescence (Handbook of Fluorescent Probes and Research Chemicals, 5th Edition, MOLECULAR PROBES, INC., 1992).

This rhodamine fluorescence has the maximum absorption (molar extinction coefficient of 63,000) at 546 nm and maximum fluorescence at 579 nm in methanol.

Further fluorescence dye suitably applicable in the present invention include aromatic heterocyclic compounds or polycyclic aromatic hydrocarbons (for example, see Taiji NISHIKAWA and Keizo HIRAKI, "Fluorescence and Phosphorescence Analysis," Kyoritsu Shuppan, 1989). Particularly preferable fluorescence dyes of the kind are, for example, anthracene, naphthalene, phenanthrene, quinoline, pyrene, perylene, etc. or derivatives thereof. These type of hydrocarbon fluorescence dyes may react with the oligopeptides by using appropriate bonding group described below.

(Bonding group)

The present invention includes no specific limitation on the type of the bonding group for labeling the fluorescence dye to the N-terminal of oligopeptide. The group including the fluorescence dye may be bonded with the N-terminal amino group either without or with additional connection group of a suitable binding group.

In this case, the group including the fluorescence is preferably bonded with the N-terminal amino group, for example, by amide bonding, thioamide bonding, sulfonamide bonding, urea bonding, thiourea bonding, urethane bonding, or the like in the following form. (Fluorescence dye group)-(binding group)-N-terminal amino group There is no specific limitation on a method for introducing the binding group. For example, in the case of amide bonding, the group including the fluorescence dye preferably has an active ester group, acid chloride, or acid anhydride.

For example, in the present invention, a rhodamine fluorescence dye having an active ester group reacts with the N-terminal amino group of oligopeptide to form an amide bonding.

This reaction can be performed under mild conditions, and gives no change in oligopeptide nor fluorescence dye.

Further, if an oligopeptide has a plurality of reactive sites, reaction conditions, reagents, etc. may be suitably selected in order to enable the reaction to occur only at the N-terminal amino group as desired. Well known techniques of organic synthesis can be suitably applied to select appropriate reaction condition.

For example, one of preferred techniques is to preliminarily protect reactive ε-amino group (for example in lysine) if necessary.

In the present invention, purity and storage stability of each marker for capillary isoelectric focusing with fluorescence detection can be checked by ordinary organic analytical method such as infrared or MR spectroscopies, and also the isoelectric focusing.

Further, if necessary, they can easily be refined using high performance liquid chromatography or other purification technique. In that case high-efficiency separation and refinement becomes possible by using a reversed-phase column, particularly using a octadecyl derivatives. Detection wavelength suitably applicable is 280 nm.

In the present invention, preferred labeling can be realized, for example, by amide-bonding a rhodamine derivative to an amino group of a peptide selected from angiotensin and derivatives thereof.

(Measurement of pI)

In the present invention, pI of each marker for isoelectric focusing with fluorescence detection can be determined by performing isoelectric focusing to compare a mobility thereof with those of commercially available markers for isoelectric focusing or to directly measure pH at a position of migration of the labeled peptide.

The isoelectric focusing preferably applicable is isoelectric focusing in polyacrylamide slab gel (see Righetti, P. G., Isoelectric Focusing: Theory, Methodology and Applications, Elsevier, Amsterdam, 1983).

An ordinary method (for example, Coomassie brilliant blue-R 250 stain) can suitably be applied to detection by a staining method.

Further, fluorescence from markers can be preferably detected by ordinary fluorescence analysis method, for example a method with a densitometer (for example, Shimazu double wavelength flying spot scanning densitometer CS 9300 PC, manufactured by Shimazu Seisakusho K. K.).

(Capillary isoelectric focusing)

There is no specific limitation on capillary isoelectric focusing apparatus to which the fluorescence-labeled oligopeptides according to the present invention can be applied as markers.

Generally, fluorescence-labeled peptides stop still as concentrated at respective positions on the pH gradient formed in the focusing carrier according to respective pI's by the capillary isoelectric focusing. These positions can be checked by detecting emitted fluorescence with excitation light.

The present invention includes no specific limitation on the light source for excitation, but use of a laser capable of emitting stable light is preferred in particular.

For example, the present invention can suitably employ a helium neon laser as excitation light for the rhodamine dye, which is a fluorescence dye.

The pH gradient formed in the focusing carrier can be checked by a fluorescence detector disposed at one end of the capillary.

As explained above, the markers for isoelectric focusing with fluorescence detection according to the present invention are synthesized by bonding a group having a fluorescence dye to oligopeptides, whereby they show uniform pI's and have high stability. Accordingly, the markers can be used as those for high-sensitive analysis where isoelectric points of sample materials after migration are checked in isoelectric focusing, based on the pH gradient formed in the focusing carrier.

Hence, the markers for isoelectric focusing with fluorescence detection according to the present invention can also preferably be applied to the capillary isoelectric focusing method.

The present invention will be explained in further detail, based on examples thereof, but it should be noted that the present invention is not intended to be limited to the examples but may involve all applications and modifications within the scope not departing from the essence of the invention.

EXAMPLES (Synthesis of Markers for Isoelectric Focusing With Fluorescence Detection)

Labeling of oligopeptides with 5-carboxytetramethylrhodamine succinimidyl ester:

Oligopeptides used in the reaction were purchased from Sigma Co., and were subjected to the following reaction with 5-carboxytetramethylrhodamine succinimidyl ester without further being refined. The oligopeptides used in the reaction were angiotensin I (asparaginic acid-arginine-valine-tyrosine-isoleucine-histidine-proline-phenylalanine-histidine-leucine, Asp-Arg-Val-Tyr-Ile-His-Pro-Phe-His-Leu) (SEQ ID NO:3), angiotensin II (asparaginic acid-arginine-valine-tyrosine-isoleucine-histidine-proline-phenylalanine, Asp-Arg-Val-Tyr-Ile-His-Pro-Phe) (SEQ ID NO:4), derivative of the foregoing two, i.e. des-asparaginic acid$^1$-angiotensin I (arginine-valine-tyrosine-isoleucine-histidine-proline-phenylalanine-histidine-leucine, Arg-Val-Tyr-Ile-His-Pro-Phe-His-Leu) (SEQ ID NO:1) and [asparagine$^1$-valine$^5$]-angiotensin II (asparagine-arginine-valine-tyrosine-valine-histidine-proline-phenylalanine, Asn-Arg-Val-Tyr-Val-His-Pro-Phe) (SEQ ID NO:2), and fibronectin fragment (glycine-arginine-glycine-asparaginic acid, Gly-Arg-Gly-Asp) (SEQ ID NO:5).

Further, the below oligopeptides were synthesized based on the Boc process by a peptide automatic synthesizing apparatus manufactured by Applied Biosystems Co. (for example, see Lectures on Chemical Experiments 1, Proteins VI, compiled by the Japanese Biochemical Society, 1992), and the oligopeptides obtained were refined by high performance liquid chromatography. The conditions used for high performance liquid chromatography were as follows: YMC-Pack ODS-AM (a column available from YMC Co., 30 mm in inner diameter×250 mm in total length); the flow rate 20 ml/min; the detection wavelength 220 nm; the mobile phase was acetonitrile gradient-0.1% trifluoroacetic acid, wherein the gradient was set to the following conditions depending upon the oligopeptides. Tyrosine-histidine-arginine-arginine (Tyr-His-Arg-Arg) (SEQ ID NO:6), 0.5% to 5%; tyrosine-tyrosine-histidine-arginine-arginine (Tyr-Tyr-His-Arg-Arg) (SEQ ID NO:7), 1% to 15%; tyrosine-tyrosine-histidine-lysine-arginine (Tyr-Tyr-His-Lys-Arg) (SEQ ID NO:8), 1% to 15%; glutamic acid-histidine-lysine-arginine (Glu-His-Lys-Arg) (SEQ ID NO:9), 0.5% to 5%; tyrosine-tyrosine-histidine-histidine (Tyr-Tyr-His-His) (SEQ ID NO:10), 1% to 15%; tyrosine-histidine-histidine (Tyr-His-His), 1% to 10%; asparaginic acid-glutamic acid-tyrosine-histidine-lysine-arginine (Asp-Glu-Tyr-His-Lys-Arg) (SEQ ID NO:11), 1% to 15%; tyrosine-histidine (Tyr-His), 1% to 15%; asparaginic acid-asparaginic acid-asparaginic acid-asparaginic acid-asparaginic acid-arginine (Asp-Asp-Asp-Asp-Asp-Arg) (SEQ ID NO:12), 1% to 15%; glycine-histidine-arginine-arginine (Glu-His-Arg-Arg) (SEQ ID NO:13), 1% to 18%; asparaginic acid-glutaminic acid-histidine-arginine-arginine-arginine (Asp-Glu-His-Arg-Arg-Arg) (SEQ ID NO:14), 0% to 15%; glutaminic acid-histidine-histidine-histidine-lysine-arginine (Glu-His-His-His-Lys-Arg) (SEQ ID NO:15), 0% to 15%; histidine-histidine-histidine-histidine-histidine (His-His-His-His-His-His) (SEQ ID NO:16), 0% to 10%; asparagic acid-histidine-histidine-arginine (Asp-His-His-Arg) (SEQ ID NO:17), 0% to 5%; asparagic acid-asparagic acid-glutamic acid-histidine-histidine-histidine-lysine-arginine (Asp-Asp-Glu-His-His-His-Lys-Arg) (SEQ ID NO:18), 0% to 15%; asparagic acid-asparagic acid-asparagic acid-asparagic acid-glutamic acid-glutamic acid-histidine-arginine-arginine-arginine-arginine-arginine (Asp-Asp-Asp-Asp-Glu-Glu-His-Arg-Arg-Arg-Arg-Arg) (SEQ ID NO:19), 0% to 15%; asparagic acid-asparagic acid-asparagic acid-glutamic acid-histidine-arginine-arginine (Asp-Asp-Asp-Glu-His-His-Arg-Arg) (SEQ ID NO:20), 0% to 15%; asparagic acid-asparagic acid-asparagic acid-glutamic acid-glutamic acid-glutamic acid-histidine-arginine-arginine-arginine (Asp-Asp-Asp-Glu-Glu-Glu-His-Arg-Arg-Arg) (SEQ ID NO:21), 1% to 15%; and asparagic acid-glutamic acid-arginine (Asp-Glu-Arg), 0% to 4%.

Each oligopeptide was dissolved in 0.1M 2-(N-Morpholino) ethanesulfonic Acid (MES)-NaOH buffer (pH 6) at a concentration of 1 mM.

5-carboxytetramethylrhodamine succinimidyl ester (purchased from MOLECULAR PROBES Co.) was dissolved in dimethylformamide at a concentration of 25 mM.

To 20 μl of each oligopeptide solution, 5 μl of the 5-carboxytetramethylrhodamine succinimidyl ester solution was added at 27C and the mixture was allowed to react overnight. To stop the reaction, 50 μl of 1M Tris-HCl buffer solution (pH 8) was added to the mixture.

The labeled oligopeptides were separated and refined by high performance liquid chromatography under the following conditions.

Column: TSKgel ODS-80T$_s$ (purchased from TOSOH CORP, 4.6 mm in inner diameter×25 cm in total length) and TSKguardgel ODS-80T$_s$ (available from TOSOH CORP, 3.2 mm in inner diameter×1.5 cm in total length)

Mobile phase: 5% to 55% acetonitrile gradient-0.1% trifluoroacetic acid

Flow rate: 1 ml/min

Detection wavelength: 280 nm

FIG. 1,2,3 and 4 show chromatograms and aimed peaks for the fourteen peptides labeled with the fluorescent material, thus obtained.

(pI's of the Fourteen Peptides Labeled With the Fluorescent Material)

The 24 fluorescence-labeled oligopeptides thus obtained were subjected to isoelectric focusing using polyacrylamide slab gel (4.2% T, 4.8% C, 55 mm×120 mm large, 0.5 mm thick) containing 2.5% carrier ampholyte (40% solution, pH 3.5–10, purchased from Pharmacia LKB Co.), and mobilities thereof were compared with those of isoelectric focusing markers commercially available (pI calibration kit 3–10, purchased from Pharmacia Biotech Co.).

The focusing conditions were as follows: started at 50 mV and focusing the voltage was increased at intervals of 15 minutes to 100 V, 200 V, 400 V, and 600 V.

After focusing, fluorescence-labeled oligopeptides in the gel were photographed through an orange filter under illumination with ultraviolet light, thereby checking focusing positions thereof.

After that, in order to know focusing positions of the commercially available isoelectric focusing markers, the gel was fixed with 20% trifluoroacetic acid for 20 minutes, then the gel was stained for 20 minutes with 0.05% of Celva violet 49 (purchased from Celva Inc.) in a mixed solvent of 25% methanol and 10% of acetic acid in water.

After staining, de-stained with a mixed solvent of methanol and acetic acid to obtain a clear background, thereby checking the focusing positions.

Figure 5:
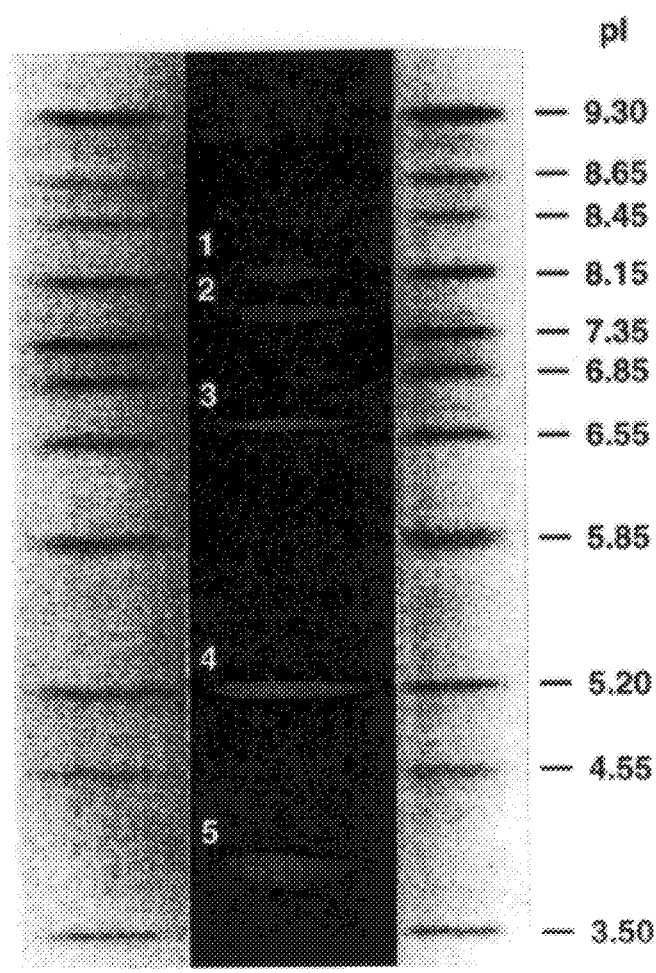
FIG. 5 is a drawing to show a migration image after isoelectric focusing of five types of fluorescence-labeled peptides(1–5) according to the present invention and isoelectric focusing markers commercially available.
Figure 6:
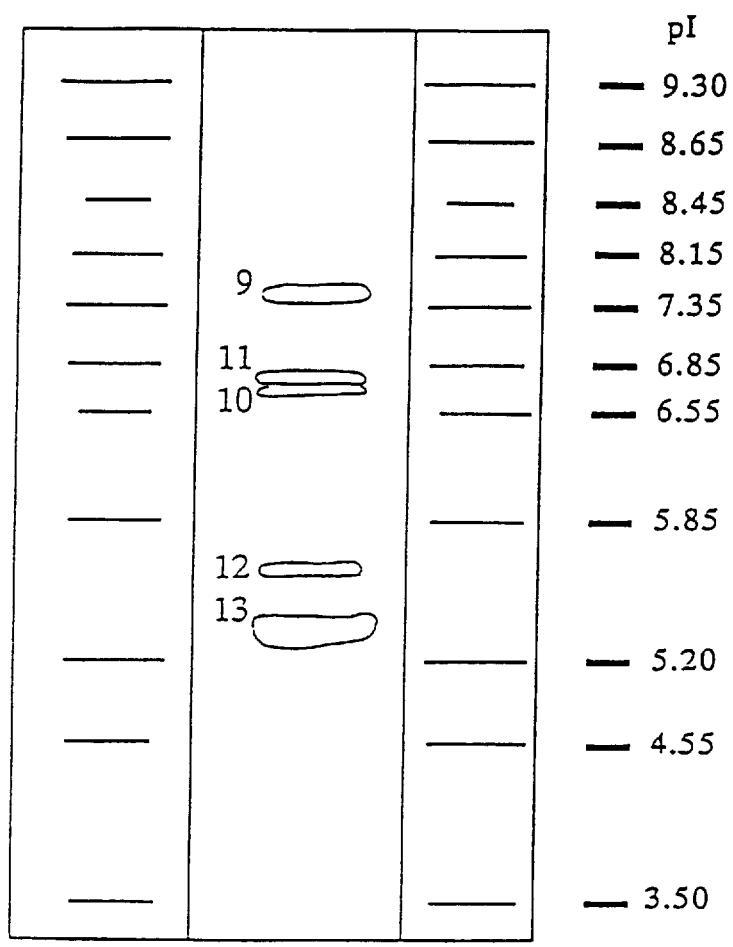
FIG. 6 is a drawing to show a migration image after isoelectric focusing of five types of fluorescence-labeled peptides(9–13) according to the present invention and isoelectric focusing markers commercially available.
Figure 7:
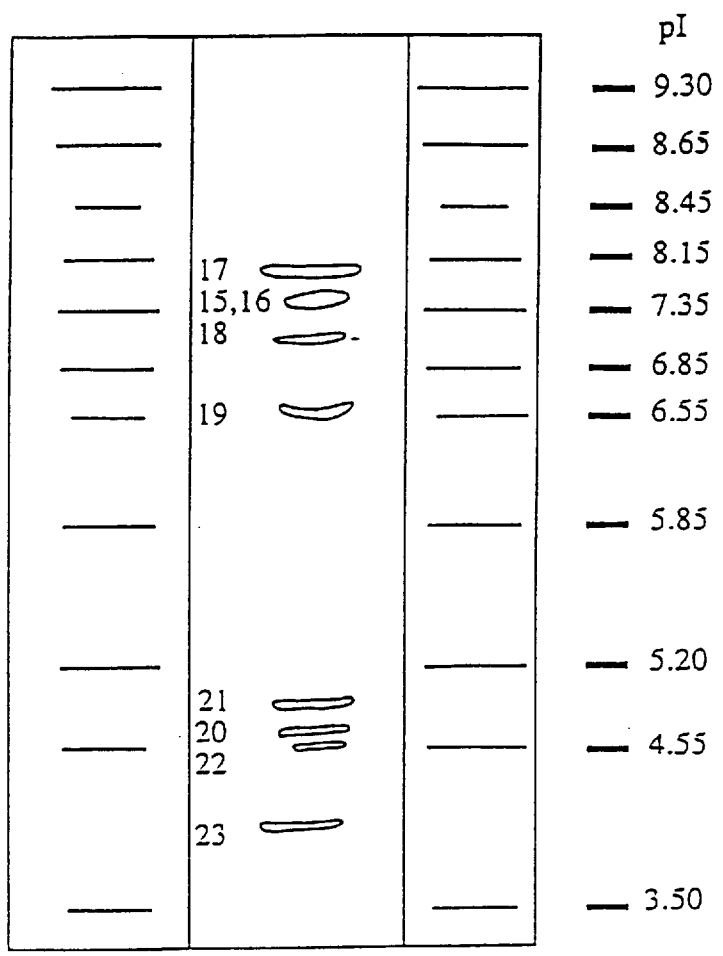
FIG. 7 is a drawing to show a migration image after isoelectric focusing of five types of fluorescence-labeled peptides(15–23) according to the present invention and isoelectric focusing markers commercially available.

FIG. 5,6,and 7 show the focusing positions of the 24 fluorescence-labeled oligopeptides obtained and the isoelectric focusing markers commercially available.

Table 1 is a list of pI's and calculation values calculated based on Eq. (1) for the respective fluorescence-labeled oligopeptides obtained (numbers 1–24). The table summarized the calculated pI's of other type of oligopeptides having wide range of pI values (numbers 25–69).

TABLE 1

| No | Structure | Calculated | Observed |
|----|-----------|------------|----------|
| 1 | (SEQ ID NO: 1)<br>Arg—Val—Tyr—Ile—His—Pro—Phe—His—Leu | 8.28 | 8.20 |
| 2 | (SEQ ID NO: 2)<br>Asn—Arg—Val—Tyr—Val—His—Pro—Phe | 8.14 | 7.75 |
| 3 | (SEQ ID NO: 3)<br>Asp—Arg—Val—Tyr—Ile—His—Pro—Phe—His—Leu | 6.46 | 6.65 |
| 4 | (SEQ ID NO: 4<br>Asp—Arg—Val—Tyr—Ile—His—Pro—Phe | 5.30 | 5.20 |
| 5 | (SEQ ID NO: 5)<br>Gly—Arg—Gly—Asp | 3.78 | 3.95 |
| 6 | (SEQ ID NO: 6)<br>Tyr—His—Arg—Arg | 11.00 | >9.30(*1) |
| 7 | (SEQ ID NO: 7)<br>Tyr—Tyr—His—Arg—Arg | 9.80 | >9.30(*1) |
| 8 | (SEQ ID NO: 8)<br>Tyr—Tyr—His—Lys—Arg | 9.62 | >9.30(*1) |
| 9 | (SEQ ID NO: 9)<br>Glu—His—Lys—Arg | 8.34 | 7.65 |
| 10 | (SEQ ID NO: 10<br>Tyr—Tyr—His—His | 6.46 | 6.70 |
| 11 | Tyr—His—His | 6.46 | 6.75 |
| 12 | (SEQ ID NO: 11)<br>Asp—Glu—Tyr—His—Lys—Arg | 5.56 | 5.55 |
| 13 | Tyr—His | 5.04 | 5.35 |
| 14 | (SEQ ID NO: 12)<br>Asp—Asp—Asp—Asp—Asp—Arg | 3.18 | <3.50(*1) |
| 15 | (SEQ ID NO: 13)<br>Glu—His—Arg—Arg | 9.34 | 7.55 |
| 16 | (SEQ ID NO: 14)<br>Asp—Glu—His—Arg—Arg—Arg | 9.24 | 7.55 |
| 17 | (SEQ ID NO: 15)<br>Glu—His—His—Lys—Arg | 8.58 | 7.90 |
| 18 | (SEQ ID NO: 16)<br>His—His—His—His—His—His | 7.16 | 7.10 |

TABLE 1-continued

| No | Structure | Calculated | Observed |
|---|---|---|---|
| 19 | (SEQ ID NO: 17)<br>Asp—His—His—Arg | 6.46 | 6.55 |
| 20 | (SEQ ID NO: 18)<br>Asp—Asp—Glu—His—His—His—Lys—Arg | 6.18 | 4.70 |
| 21 | (SEQ ID NO: 19<br>Asp—Asp—Asp—Asp—Glu—Glu—His—Arg—Arg—Arg—Arg—Arg | 4.88 | 4.90 |
| 22 | (SEQ ID NO: 20)<br>Asp—Asp—Asp—Glu—His—His—Arg—Arg | 4.62 | 4.55 |
| 23 | (SEQ ID NO: 21)<br>Asp—Asp—Asp—Glu—Glu—Glu—His—Arg—Arg | 4.26 | 4.05 |
| 24 | Asp—Glu—Arg | 3.66 | <3.50(*1) |
| 25 | (SEQ ID NO: 31)<br>Glu—His—Arg—Arg—Arg | 12.20 | — |
| 26 | (SEQ ID NO: 32)<br>Tyr—His—Lys—Arg—Arg | 11.28 | — |
| 27 | (SEQ ID NO: 33)<br>Glu—His—His—Lys—Arg—Arg | 11.20 | — |
| 28 | (SEQ ID NO: 34)<br>Glu—Tyr—Tyr—His—His—Lys—Arg—Arg—Arg | 10.24 | — |
| 29 | (SEQ ID NO: 35)<br>Glu—His—His—Lys—Lys—Arg | 10.20 | — |
| 30 | (SEQ ID NO: 29<br>Tyr—His—Lys—Arg | 10.00 | — |
| 31 | (SEQ ID NO: 36)<br>Asp—Tyr—His—Lys—Arg—Arg | 10.00 | — |
| 32 | (SEQ ID NO: 37)<br>Asp—Glu—Tyr—His—lys—Arg—Arg—Arg | 10.00 | — |
| 33 | (SEQ ID NO: 38)<br>Asp—Tyr—Tyr—His—Lys—Arg—Arg | 9.62 | — |
| 34 | (SEQ ID NO: 39)<br>Asp—Glu—Tyr—Tyr—His—His—Lys—Arg—Arg—Arg | 9.60 | — |
| 35 | (SEQ ID NO: 40)<br>Glu—His—His—Arg—Arg | 9.48 | — |
| 36 | (SEQ ID NO: 41) | 9.34 | — |
| 37 | (SEQ ID NO: 42)<br>Glu—His—His—Lys—Arg | | |
| 38 | (SEQ ID NO: 43)<br>Asp—Glu—Tyr—His—His—Arg—Arg—Arg | 8.28 | — |
| 39 | (SEQ ID NO: 44)<br>Tyr—Tyr—His—His—His—Arg | 8.22 | — |
| 40 | (SEQ ID NO: 45)<br>Asp—Glu—Tyr—His—Arg—Arg—Arg | 8.14 | — |
| 41 | Tyr—His—Arg | 8.14 | — |
| 42 | (SEQ ID NO: 46)<br>Tyr—Tyr—Tyr—His—His—Arg | 8.14 | — |
| 43 | (SEQ ID NO: 47)<br>Tyr—Tyr—His—His—Arg | 8.14 | — |
| 44 | (SEQ ID NO: 48)<br>Glu—Tyr—His—Lys—Arg | 8.06 | — |
| 45 | (SEQ ID NO: 49)<br>Asp—Asp—Tyr—His—His—Lys—Arg—Arg | 8.06 | — |
| 46 | (SEQ ID NO: 50)<br>Asp—Tyr—His—Lys—Arg | 8.06 | — |
| 47 | Tyr—His—Lys | 8.06 | — |
| 48 | (SEQ ID NO: 48)<br>Glu—Tyr—His—Lys—Arg | 8.05 | — |
| 49 | (SEQ ID NO: 51)<br>Tyr—Tyr—Tyr—His—His—Arg | 8.04 | — |
| 50 | (SEQ ID NO: 52)<br>Tyr—Tyr—His—Arg | 7.98 | — |
| 51 | (SEQ ID NO: 53)<br>Tyr—Tyr—His—Lys—Arg | 7.94 | — |
| 52 | (SEQ ID NO: 54)<br>Tyr—Tyr—Tyr—His—Arg | 7.90 | — |
| 53 | (SEQ ID NO: 55)<br>His—His—His—His—His | 7.06 | — |
| 54 | (SEQ ID NO: 56)<br>Asp—His—His—His—Arg | 6.94 | — |
| 55 | (SEQ ID NO: 57)<br>His—His—His—His | 6.94 | — |
| 56 | (SEQ ID NO: 58)<br>Asp—His—His—His—Arg | 6.76 | — |
| 57 | Tyr—Tyr—Arg | 6.55 | — |
| 58 | (SEQ ID NO: 59)<br>Asp—Glu—His—His—Arg—Arg | 6.48 | — |
| 59 | (SEQ ID NO: 60)<br>Asp—Asp—Glu—Tyr—His—His—Lys—Arg—Arg | 6.48 | — |

TABLE 1-continued

| No | Structure | Calculated | Observed |
|---|---|---|---|
| 60 | (SEQ ID NO: 61)<br>Tyr—Tyr—Tyr—Arg | 6.48 | — |
| 61 | (SEQ ID NO: 62)<br>Asp—Asp—Glu—Tyr—His—Lys—Arg—Arg | 5.60 | — |
| 62 | Asp—His—Arg | 5.30 | — |
| 63 | (SEQ ID NO: 63)<br>Asp—Asp—Asp—Glu—Lys—Arg—Arg—Arg | 4.64 | — |
| 64 | (SEQ ID NO: 64)<br>Asp—Asp—Asp—Asp—His—His—Arg—Arg | 4.50 | — |
| 65 | (SEQ ID NO: 65)<br>Asp—Glu—Arg—Arg | 4.36 | — |
| 66 | (SEQ ID NO: 66)<br>Asp—Glu—Glu—Lys—Arg | 4.12 | — |
| 67 | (SEQ ID NO: 67)<br>Asp—Asp—Glu—Arg | 3.46 | — |
| 68 | (SEQ ID NO: 68)<br>Asp—Asp—Asp—Arg | 3.38 | — |
| 69 | (SEQ ID NO: 69)<br>Asp—Asp—Asp—Asp—Arg | 3.28 | — |

(*1)The position of the fluorescent-labeled oligopeptide was out of the range (pI 9.30–3.5). (Capillary isoelectric focusing with fluorescence detection)

Then the fourteen fluorescence-labeled oligopeptides obtained were subjected to separation and detection by capillary isoelectric focusing with fluorescence detection (Hjerten, S., Journal of Chromatography, 347, 191–198, 1985).

Used was a fused silica capillary (purchased from GL Science Co.) of the inner diameter 75 μm, the outer diameter 375 μm, and the total length 6 cm, was coated with linear polyacrylamide on its inner wall.

The capillary filled with a sample solution, fluorescence-labeled peptides containing 1% ampholine and 0.1% Tween 20.

The anolyte was 10 mM phosphoric acid solution containing 2% of methyl cellulose (the viscosity of the 2% solution at 25° C.; 4,000 cP, purchased from Sigma Co.), and the catholyte was 20 mM NaOH solution containing 2% of hydroxypropylmethyl cellulose (the viscosity of 2% solution at 25° C.; 4,000 cP, purchased from Sigma Co.). Focusing was carried out for 2 min with high-voltage power supply at the maximum of either 2.4 kV or 10 μA.

Focused fluorescence-labeled peptides were mobilized towards the detection window electrophoretically.

The helium neon laser (wavelength 543.5 nm, power 1 mW, Model; 05-LGR-151-S, purchased from Melles Griot Co.) was used for excitation. Fluorescence was collected by a 40× objective lens, then the fluorescence intensity was measured by use of photomultiplier tube(Model; R1387, manufactured by Hamamatsu Photonics K.K.) after filtration with bandpass filter (590 nm, 30 mm band width, Model DIF-BP-3, manufactured by Nippon Sinkuu, Kogaku) and a cut-off filter(Model SCF-50S-560, manufactured by Sigma Kouki), and the data were collected using an integrator (Model CR4A, manufactured by Shimazu Seisakusho K.K.).

Figure 8:
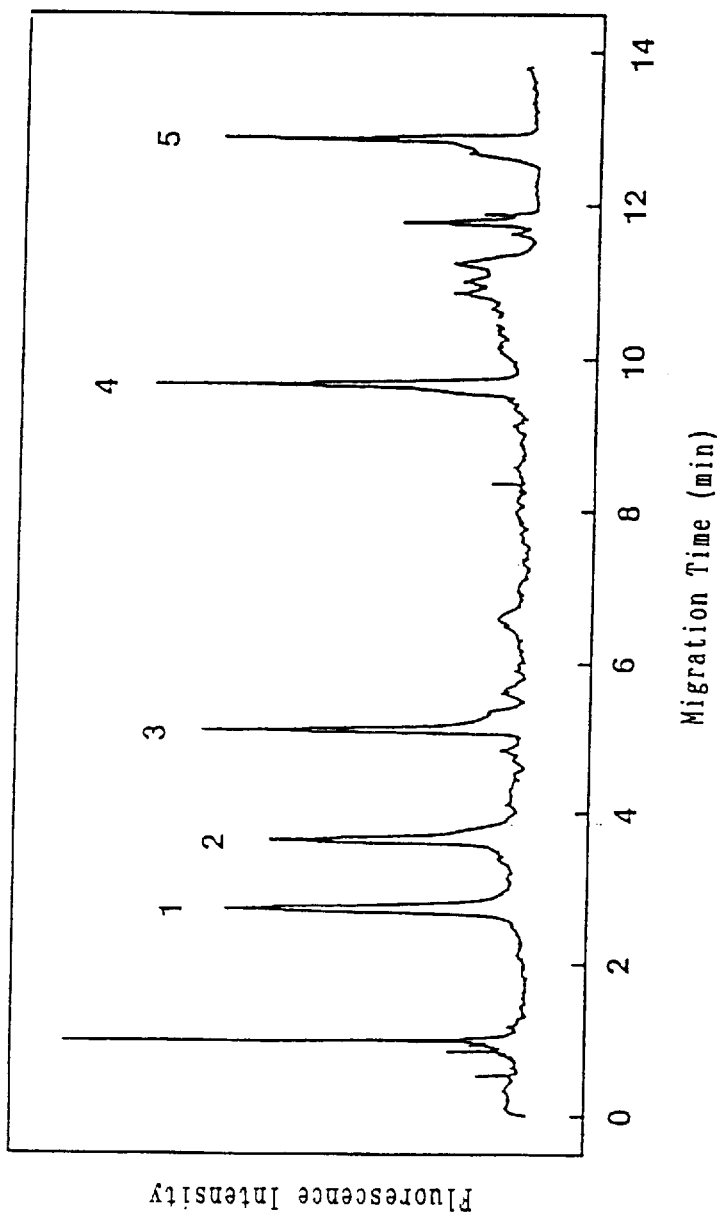
FIG. 8 is a drawing to show a relation between migration period and fluorescence intensity for five types of fluorescence-labeled peptides(1–5) when fluorescence capillary isoelectric focusing is carried out.

FIG. 8 shows moving periods and fluorescent intensities in the capillary isoelectric focusing with fluorescence detection, of five peptides out of 24 fluorescence-labeled peptides obtained.

As seen from the above results, it was confirmed that the present invention was able to provide the fluorescence-labeled oligopeptides by binding a fluorescence dye to oligopeptides. Since the fluorescence dye is bonded to the oligopeptides under mild conditions, the reaction causes no damage on the oligopeptides and the fluorescent material, the number of fluorescent materials and locations thereof bonded to the oligopeptides can be specified, and the obtained oligopeptides containing the fluorescence dye will have highly stable, uniform, and unique pI's. Accordingly, the markers for capillary isoelectric focusing with fluorescence detection obtained in the present invention can be used as markers for estimating isoelectric points of sample materials.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 76873/1995 filed on Mar. 31, 1995 and No. 271196/1995 filed on Oct. 19, 1995 are hereby incorporated by reference.

What is claimed is:

1. An isoelectric point marker for isoelectric focusing with fluorescence detection, which is an oligopeptide selected from the group consisting of Asp-His-His-Arg (SEQ ID NO:17), Arg-Asp-Asp-Asp-Asp-Asp (SEQ ID NO:27), Glu-His-Arg-Arg-Arg (SEQ ID NO:31), Glu-His-His-Lys-Arg-Arg (SEQ ID NO:33), Glu-Tyr-Tyr-His-His-Lys-Arg-Arg-Arg (SEQ ID NO:34), Glu-His-His-Lys-Lys-Arg (SEQ ID NO:35), Asp-Tyr-His-Lys-Arg-Arg (SEQ ID NO:36), Asp-Glu-Tyr-His-Lys-Arg-Arg-Arg (SEQ ID NO:37), Asp-Tyr-Tyr-His-Lys-Arg-Arg (SEQ ID NO:38), Asp-Glu-Tyr-Tyr-His-His-Lys-Arg-Arg-Arg (SEQ ID NO:39), Glu-His-His-Arg-Arg (SEQ ID NO:40), Asp-Glu-Tyr-Tyr-Tyr-His-His-Lys-Lys-Arg-Arg (SEQ ID NO:41), Glu-His-His-Lys-Arg (SEQ ID NO:42), Asp-Glu-Tyr-His-His-Arg-Arg-Arg (SEQ ID NO:43), Tyr-Tyr-His-His-His- Arg (SEQ ID NO:44), Asp-Glu-Tyr-His-Arg-Arg-Arg (SEQ ID NO:45), Tyr-His-Arg, Tyr-Tyr-Tyr-His-His-His-Arg (SEQ ID NO:46), Tyr-Tyr-His-His-Arg (SEQ ID NO:7), Glu-Tyr-His-Lys-Arg (SEQ ID NO:48), Asp-Asp-Tyr-His-Lys-Arg-Arg (SEQ ID NO:49), Asp-Tyr-His-Lys-Arg (SEQ ID NO:50), Tyr-His-Lys, Tyr-Tyr-Tyr-His-His-Arg (SEQ ID NO:51), Tyr-Tyr-His-Arg (SEQ ID NO:52), Tyr-Tyr-Tyr-His-Arg (SEQ ID NO:54), Asp-His-His-His-His-Arg (SEQ ID NO:56), Asp-Glu-His-His-Arg-Arg (SEQ ID NO:59), Asp-Asp-Glu-Tyr-His-His-Lys-Arg-Arg (SEQ ID NO:60), Tyr-Tyr-Tyr-Arg (SEQ ID NO:61), Asp-Asp-Glu-Tyr-His-Lys-Arg-Arg (SEQ ID NO:62), Asp-Asp-Asp-Glu-Lys-Arg-Arg (SEQ ID NO:63), Asp-Asp-Asp-Asp-His-His-Arg-Arg (SEQ ID NO:64), Asp-Glu-Arg-Arg (SEQ ID NO:65), Asp-Glu-Glu-Lys-Arg (SEQ ID NO:66), and Asp-Asp-Glu-Arg (SEQ ID NO:67); bonded to a fluorescence dye.

2. The marker for isoelectric focusing with fluorescence detection according to claim 1, wherein said fluorescence dye is bonded to an amino group of N-terminal amino acid of said oligopeptide.

3. The marker for isoelectric focusing with fluorescence detection according to claim 2, wherein said said fluorescence dye is bonded to said oligopeptide by a bond selected from the group consisting of amide, thioamide, sulfonamide, urea, thiourea, and urethane.

4. The marker for isoelectric focusing with fluorescence detection according to claim 1, wherein said fluorescence dye is selected from the group consisting of rhodamine, fluorescein, cyanine, indocyanine, indocarbocyanine, pyronine, lucifer yellow, quinacrine, squarillium, coumarin, fluoroanthranilmaleimide, and anthracene.

5. The marker for isoelectric focusing with fluorescence detection according to claim 1, wherein said isoelectric focusing with fluorescence detection is a capillary isoelectric focusing with fluorescence detection.

6. The marker for isoelectric focusing with fluorescence detection according to claim 1, wherein said oligopeptide is selected from the group consisting of Asp-His-His-Arg (SEQ ID NO:17), Glu-His-His-Lys-Arg (SEQ ID NO:42), Asp-Glu-Tyr-His-His-Arg-Arg-Arg (SEQ ID NO:43), Tyr-Tyr-His-His-His-Arg (SEQ ID NO:44), and Asp-Glu-Glu-Lys-Arg (SEQ ID NO:66).

7. A method of measuring isoelectric point (pI) of a substance by isoelectric focusing comprising:

(a) forming a pH gradient in a focusing carrier with a standard comprising the isoelectric point marker according to claim 1, (b) focusing said substance to stop in the carrier at a position equal to the isoelectric point of said substance, and (c) determining the isoelectric point of said substance by fluorescence detection of the standard.

8. The method of pI measurement according to claim 7, wherein isoelectric focusing is effected in a capillary tube.

9. The method of pI measurement according to claim 7, wherein said capillary tube has an inner diameter of 5 µm to 100 µm and a length of 30 cm to 100 cm.

10. The method of pI measurement according to claim 7, wherein said substance is a peptide or protein.

11. The method of pI measurement according to claim 7, in which the fluorescence dye is excited by laser light.

12. The method of pI measurement according to claim 7, wherein isoelectric focusing is effected in a slab gel.

13. A method of measuring isoelectric point (pI) of a substance by isoelectric focusing comprising:

(a) forming a pH gradient in a focusing carrier with a standard comprising the isoelectric point marker according to claim 9, (b) focusing said substance to stop in the carrier at a position equal to the isoelectric point of said substance, and (c) determining the isoelectric point of said substance by fluorescence detection of the standard.

14. The method of pI measurement according to claim 13, wherein isoelectric focusing is effected in a capillary tube.

15. The method of pI measurement according to claim 13, wherein said capillary tube has an inner diameter of 5 µm to 100 µm and a length of 30 cm to 100 cm.

16. The method of pI measurement according to claim 13, wherein said substance is a peptide or protein.

17. The method of pI measurement according to claim 13, in which the fluorescence dye is excited by laser light.

18. The method of pI measurement according to claim 13, wherein isoelectric focusing is effected in a slab gel.

* * * * *